US012215311B2

(12) United States Patent
Kim

(10) Patent No.: US 12,215,311 B2
(45) Date of Patent: Feb. 4, 2025

(54) SPIRULINA PLATENSIS STRAIN

(71) Applicant: N-CELL CO., LTD., Chungcheongbuk-do (KR)

(72) Inventor: Zun Kim, Naju-si (KR)

(73) Assignee: N-CELL CO., LTD., Chungcheongbuk-Do (KR)

( * ) Notice: Subject to any disclaimer, the term of this patent is extended or adjusted under 35 U.S.C. 154(b) by 412 days.

(21) Appl. No.: 17/292,284

(22) PCT Filed: Aug. 28, 2020

(86) PCT No.: PCT/KR2020/011580
§ 371 (c)(1),
(2) Date: May 2, 2022

(87) PCT Pub. No.: WO2021/040472
PCT Pub. Date: Mar. 4, 2021

(65) Prior Publication Data
US 2022/0364043 A1 Nov. 17, 2022

(30) Foreign Application Priority Data
Aug. 30, 2019 (KR) .................. 10-2019-0107268

(51) Int. Cl.
*C12N 1/20* (2006.01)
*C12N 1/02* (2006.01)
*C12N 1/12* (2006.01)
(52) U.S. Cl.
CPC ............... *C12N 1/205* (2021.05); *C12N 1/02* (2013.01); *C12N 1/125* (2021.05)

(58) Field of Classification Search
CPC . C12N 1/125; C12N 1/02; C12N 1/20; C12N 1/205; C12N 1/12; C12R 2001/01; C12R 2001/89
See application file for complete search history.

(56) References Cited

FOREIGN PATENT DOCUMENTS

| CN | 101705188 A | 5/2010 |
|---|---|---|
| CN | 106566787 A | 4/2017 |
| KR | 10-2019-0012647 A | 2/2019 |

OTHER PUBLICATIONS

Rout, NP et al. Divergence in three newly identified Arthrospira species from Mexico. World J. Microbiol. Biotechnol. 2015. 31: 1157-1165. (Year: 2015).*
Wang, Zhi Ping et al. "Morphological reversion of *Spirulina* (arthrospira) *platensis* (cyanophyta): from linear to helical", Journal of Phycology, 2005, vol. 41, pp. 622-628.
Mishra, Tulika et al. "Spirulina: the beneficial algae". International Journal of Applied Microbiology Science. 2013, vol. 2, No. 3, pp. 21-35.
Rossi, N. et al., "Harvesting of cyanobacterium arthospira platensis using inorganic filtration membranes", Separation Science and Technology, vol. 40, No. 15, Nov. 1, 2005 (Nov. 1, 2005), pp. 3033-3050, XP093001817, ISSN: 1449-6395, DOI: 10.1080/01496390500385046.

* cited by examiner

*Primary Examiner* — David W Berke-Schlessel
*Assistant Examiner* — Susan E. Fernandez
(74) *Attorney, Agent, or Firm* — Bridgeway IP Law Group, PLLC; Sang Ho Lee; Hyun Woo Shin

(57) ABSTRACT

The present invention relates to a novel *Spirulina* strain having a linear shape, which *Spirulina* strain can be used to achieve a harvest of *Spirulina* strain with high yield.

7 Claims, 3 Drawing Sheets

SPIRULINA PLATENSIS STRAIN

TECHNICAL FIELD

The present invention relates to a novel *Spirulina* strain having a long linear shape and a method for harvesting a *Spirulina* strain using the novel *Spirulina* strain.

BACKGROUND ART

*Spirulina*, a type of blue-green algae growing naturally through photosynthesis on the surface of lakes high in alkalinity and salinity in tropical regions, is a high protein food that has a protein content of more than 65%. In addition, the amino acids that make up the protein contained in the *Spirulina* include all essential amino acids indispensable for living organisms to survive, and the contents of lipids (6-10%) and carbohydrates (15-20%) in *Spirulina* are relatively low, making the *Spirulina* available as a food resource. Besides, *Spirulina* contains a large amount of edible pigments having antioxidant activity, such as beta-carotene (provitamin A) or phycocyanin, and is rich in various types of vitamins, minerals, and fibers. As the *Spirulina* is a prokaryotic organization that lacks cellulose in its cell wall and thus has 90% of its cytoplasm digestible, it is considered as an important food resource with high utilization efficiency and has recently been in the spotlight as a health supplement.

In particular, the *Spirulina* strains cultured in a closed tank such as a light incubator have a higher protein content than those cultured outdoor such as in a pond or open fields. The protein content of *Spirulina* strains cultured in a light incubator is 65 to 75%, while that of *Spirulina* strains cultured in open fields is less than 60%. It is therefore expected to produce high-quality *Spirulina* with high protein content by pure cultivation of *Spirulina* using a closed tank like a light incubator.

Even when the *Spirulina* is cultivated in a closed tank such as a light incubator, it is very difficult to harvest the *Spirulina* by centrifugation, which requires a high initial facility cost, with a limit on the amount of labor, and constant manpower and allows only a limited wash after harvest. Otherwise, when the *Spirulina* is harvested using a sieve, the harvest efficiency is too low to achieve a harvest with ease, for the conventional *Spirulina* has a short spiral shape in a micrometer size of 0.3 mm or less.

In addition, although $NH_4Cl$ is known as a good nitrogen source that boosts the initial growth rate during the culture of *Spirulina*, it rather hinders the growth of the conventional *Spirulina* strain, which has poor resistance to ammonia produced by $NH_4Cl$ used at high concentration as a nitrogen source for *Spirulina*. Hence, the good nitrogen source for the culture of *Spirulina*, $NH_4Cl$ has to be used only limitedly in the culture of *Spirulina* and has been substituted by $NaNO_3$, urea, or the like.

Accordingly, the inventors of the present invention have been working on research for the solution to this problem and devised a way to prepare a novel *Spirulina* strain, completing the present invention.

SUMMARY OF THE DISCLOSURE

It is an object of the present invention to provide an *Arthrospira platensis* NCB002 strain having a long linear shape and deposited with accession number KCTC 13731BP.

It is another object of the present invention to provide a method for harvesting a *Spirulina* strain that includes passing an *Arthrospira platensis* NCB002 strain having a long linear shape and deposited with accession number KCTC 13731BP through a sieve having a mesh size of 0.1 to 1.0 mm.

In order to achieve the objects, the present invention provides an *Arthrospira platensis* NCB002 strain having a long linear shape and deposited with accession number KCTC 13731BP.

The present invention also provides a method for harvesting a *Spirulina* strain that includes the step of passing an *Arthrospira platensis* NCB002 strain having a linear shape and deposited with accession number KCTC 13731BP through a sieve having a mesh size of 0.1 to 1.0 mm.

In a specific embodiment of the present invention, a novel *Spirulina* strain obtained by irradiating a known *Spirulina* strain with UV radiation is named as "*Spirulina* (*Arthrospira platensis*) NCB002 strain". As confirmed in the embodiment, the *Spirulina* strain is characterized by having a linear shape with a length of 1 cm or greater, growing in the presence of an ammoniacal nitrogen source as it survives in a culture medium containing $NH_4Cl$ in an amount of 0.4 g/L or less, and being harvested through a sieve having a mesh size of 0.2 mm, so it can be harvested and washed in a shorter time without a great loss of biomass compared to the known *Spirulina* strains.

Hereinafter, the present invention will be described in further detail.

Unless otherwise defined, all technical terms used herein have the same meaning as commonly understood by those skilled in the related art.

In an aspect of the present invention, there is provided a *Spirulina* (*Arthrospira platensis*) NCB002 strain having a long linear shape and deposited with accession number KCTC 13731BP.

The inventors of the present invention cultured a naturally occurring *Spirulina* (*Arthrospira platensis*) strain in an SOT medium, exposed the cultured *Spirulina* strain to UV radiations and observed the morphology of the *Spirulina* with an optical microscope to sort out the mutant strain of *Spirulina* having a long linear shape unlike the common *Spirulina* strains using a micromanipulator. The strain was analyzed in regards to the main item for cyanobacterial identification, 16S rRNA sequence, the size and shape of filamentum, the morphology of terminal cells, and the distribution location of gas endoplasmic reticulum, and consequently identified as belonging to *Arthrospira platensis*, one of the *Spirulina* species. It was named as *Arthrospira platensis* NCB002 strain and deposited under the accession number of KCTC 13731BP in the Korean Collection for Type Cultures (KCTC) on Nov. 22, 2018.

In accordance with an embodiment of the present invention, the *Arthrospira platensis* NCB002 strain with accession number KCTC 13731BP (hereinafter *Arthrospira platensis* NCB002 strain) according to the present invention has a linear shape with a length of 1 cm or greater and survives in a culture medium containing $NH_4Cl$ in an amount of 0.4 g/L or less, while a known spiral-shaped *Spirulina* strain is 0.3 mm or less in length and unable to survive in a culture medium containing $NH_4Cl$ in an amount of 0.2 g/L or more. In other words, the *Arthrospira platensis* NCB002 strain of the present invention is capable of surviving in a culture medium containing $NH_4Cl$ in an amount of 0.1 to 0.4 g/L, preferably 0.3 to 0.4 g/L.

In accordance with another embodiment of the present invention, the *Arthrospira platensis* NCB002 strain KCTC 13731BP of the present invention is characterized by having a linear shape with a length of 0.5 to 3 cm.

$NH_4Cl$ plays a role in helping the initial growth of the *Spirulina* strain. But, when the *Spirulina* strain is cultured in a medium containing $NH_4Cl$ at high concentration, the ammonia produced by the $NH_4Cl$ inhibits the growth of the *Spirulina* strain.

Contrarily, the *Arthrospira platensis* NCB002 strain of the present invention survives even when cultured in a medium containing $NH_4Cl$ in an amount of 0.4 g/L or less, so it can be beneficially cultured with a high-concentration ammoniacal nitrogen source.

In other words, the *Arthrospira platensis* NCB002 strain is characterized by being able to survive in a culture medium containing $NH_4Cl$ in an amount of 0.1 to 0.4 g/L, preferably 0.3 to 0.4 g/L.

In another aspect of the present invention, there is provided a method for harvesting a *Spirulina* strain that includes the step of passing an *Arthrospira platensis* NCB002 strain having a linear shape and deposited with accession number KCTC 13731BP through a sieve having a mesh size of 0.1 to 1.0 mm.

The *Arthrospira platensis* NCB002 strain has a linear shape with a length of 1 cm or greater, while the known *Spirulina* strain has a short spiral shape in a micrometer size of 0.3 mm or less. It is therefore possible to obtain a more considerable amount of the novel *Arthrospira platensis* NCB002 strain than the known *Spirulina* strain through a sieve.

The novel *Spirulina* strain of the present invention has a long linear shape and survives in a culture medium containing $NH_4Cl$ in an amount of 0.4 g/L or less, so it can be harvested with high yield simply by using a sieve.

BRIEF DESCRIPTION OF THE DRAWINGS

The above and other objects, features and advantages of the present invention will be more clearly understood from the following detailed description taken in conjunction with the accompanying drawings, in which.

BEST MODE FOR CARRYING OUT THE INVENTION

Hereinafter, the present invention will be described in detail with reference to examples, comparative examples, and experimental examples, which are given for exemplary illustrations of the present invention and construed not to limit the scope of the present invention.

Example 1

Isolation and Identification of Novel *Spirulina* Strain

The novel *Spirulina* strain was obtained by mutating a known *Spirulina* strain.

Specifically, a naturally occurring *Spirulina* (*Arthrospira platensis*) strain was cultured in an SOT medium and then exposed to UV radiations. The morphology of the UV-exposed *Spirulina* strain was observed with an optical microscope during cultivation to sort out the mutant strain of *Spirulina* having a long linear shape unlike the common *Spirulina* strains using a micromanipulator.

As a result, the sorted strain was named as *Arthrospira platensis* NCB002 strain and deposited under the accession number of KCTC 13731BP in the Korean Collection for Type Cultures (KCTC) on Nov. 22, 2018.

Example 2

Cultivation of Strain

The novel *Spirulina* strain isolated and identified in Example 1 was cultured in 100 mL of an SOT medium. The composition of the SOT medium was given as presented in the following Table 1, and that of a trace metal mix added to the SOT medium was as presented in the following Table 2.

TABLE 1

| | | |
|---|---|---|
| $NaHCO_3$ | 16.8 | g |
| $K_2HPO_4$ | 0.5 | g |
| $NaNO_3$ | 2.5 | g |
| $K_2SO_4$ | 1 | g |
| NaCl | 1 | g |
| $MgSO_4 \cdot 7H_2O$ | 0.2 | g |
| $CaCl_2 \cdot 2H_2O$ | 0.04 | g |
| $FeSO_4 \cdot 7H_2O$ | 0.01 | g |
| $Na_2EDTA \cdot 2H_2O$ | 0.08 | g |
| Trace metal mix A5* | 1 | ml |
| Distilled water | 1 | L |

TABLE 2

| | | |
|---|---|---|
| $H_3BO_3$ | 2.86 | g |
| $MnCl_2 \cdot 4H_2O$ | 1.81 | g |
| $ZnSO_4 \cdot 7H_2O$ | 0.22 | g |
| $NaMoO_4 \cdot 2H_2O$ | 0.21 | g |
| $CuSO_4 \cdot 5H_2O$ | 0.08 | g |
| $CO(NO_3)_2 \cdot 6H_2O$ | 0.05 | g |
| Distilled water | 1 | L |

Figure 1:
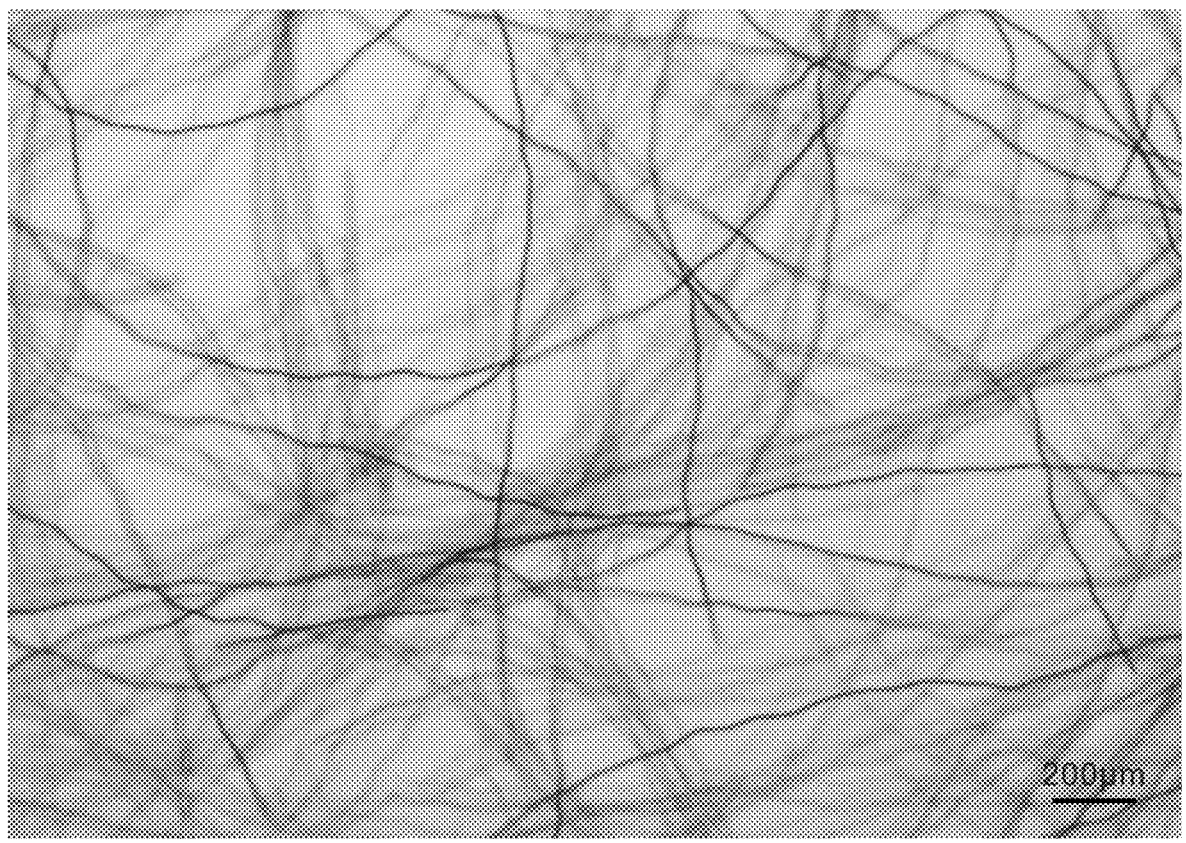
FIG. 1 is a microscopic image of the novel *Spirulina* strain culture.

On the other hand, the culture of the novel *Spirulina* strain was observed for morphology with a microscope and its microscopic image was as shown in FIG. 1.

As can be seen from FIG. 1, the novel *Spirulina* strain had a linear shape with a length of 1 cm or greater.

Examples 3 to 6

Variation of $NH_4Cl$ Concentration of Culture Medium

The procedures were performed for cultivation of *Spirulina* in the same manner as described in Example 2, excepting that the concentration of $NH_4Cl$ added to the medium for cultivation of *Spirulina* was 0.1 g/L (Example 3), 0.2 g/L (Example 4), 0.3 g/L (Example 5), or 0.4 g/L (Example 6).

Comparative Example 1

Variation of $NH_4Cl$ Concentration of Culture Medium

The procedures were performed for cultivation of *Spirulina* in the same manner as described in Example 2, excepting that the concentration of NH$_4$Cl added to the medium for cultivation of *Spirulina* was 0.5 g/L (Comparative Example 1.

Comparative Example 2

Cultivation of Spiral-Shaped *Spirulina* Strain

The known spiral-shaped *Spirulina* strain was cultured in the same manner as described in Examples 1 and 2.

Figure 2:
FIG. 2 is a microscopic image of a known spiral-shaped *Spirulina* strain culture.

On the other hand, the culture of the known spiral-shaped *Spirulina* strain was observed for morphology with a microscope and its microscopic image was as shown in FIG. 2.

Comparative Examples 3 to 7

Variation of NH$_4$Cl Concentration of Culture Medium

The procedures were performed for cultivation of the known *Spirulina* strains in the same manner as described in Comparative Example 2, excepting that the concentration of NH$_4$Cl added to the medium for cultivation of *Spirulina* was 0.1 g/L (Comparative Example 3), 0.2 g/L (Comparative Example 4), 0.3 g/L (Comparative Example 5), or 0.4 g/L (Comparative Example 6), or 0.5 g/L (Comparative Example 7).

Experimental Example 1

Resistance to NH$_4$Cl

The novel *Spirulina* strain or the spiral-shaped *Spirulina* strain was cultured in a medium containing NH$_4$Cl in the same manner as described in Examples 3 to 6 and Comparative Example 1, or Comparative Examples 3 to 7 and visually inspected in regards to viability to determine the resistance of the novel *Spirulina* strain to NH$_4$Cl. In the following Table 3, "O" indicates the strain viable, and "X" indicates the strain inviable.

As can be seen from Table 3, the novel *Spirulina* strain of the present invention was able to survive in a medium containing NH$_4$Cl in an amount of 0.1 to 0.4 g/L, while the known spiral-shaped *Spirulina* strain was unable to survive in a medium containing NH$_4$Cl in an amount of more than 0.2 g/L.

TABLE 3

| Strain type | NH$_4$Cl content (g/L) | | | | |
| --- | --- | --- | --- | --- | --- |
| | 0.1 | 0.2 | 0.3 | 0.4 | 0.5 |
| Known spirulina strain | O | O | X | X | X |
| Novel spirulina strain | O | O | O | O | X |

Experimental Example 2

Harvest of Strains

The novel *Spirulina* strain of the present invention cultures in the same manner of Examples 1 and 2 and the known *Spirulina* strain cultured in the manner of Comparative Example 2 were passed through a sieve having a mesh size of 0.2 mm for harvest.

Figure 3:
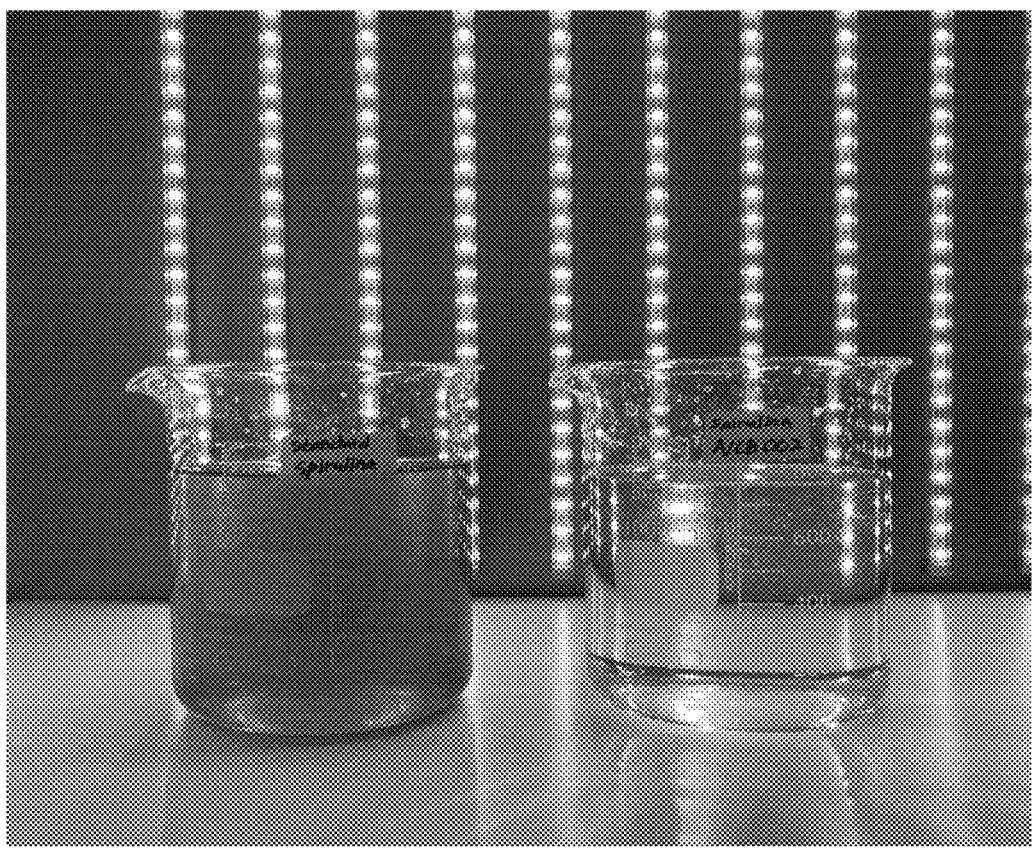
FIG. 3 shows the portions remaining after passing the novel *Spirulina* strain culture (right-sided) and the known spiral-shaped *Spirulina* strain culture (left-sided) through a sieve having a mesh size of 0.2 mm.

The culture media of the novel *Spirulina* strain and the known *Spirulina* strain remaining after passing through the sieve having a mesh size of 0.2 mm were compared as shown in FIG. 3.

As can be seen from FIG. 3, the culture medium of the novel *Spirulina* strain after passing through the sieve was clear (colorless) as the novel *Spirulina* strain did not pass through the sieve having a mesh size of 0.2 mm, while the culture medium of the known *Spirulina* strain was green as the known *Spirulina* strain successfully passed through the sieve.

MODE FOR CARRYING OUT THE INVENTION

The present invention is directed to a novel *Spirulina* strain having a long linear shape and a method for harvesting a *Spirulina* strain using the novel *Spirulina* strain.

INDUSTRIAL APPLICABILITY

The novel *Spirulina* strain having a long linear shape and the method for harvesting a *Spirulina* strain using the novel *Spirulina* strain according to the present invention are applicable to the preparation of *Spirulina*.

What is claimed is:

1. An *Arthrospira platensis* NCB002 strain having a linear shape and deposited with accession number KCTC 13731BP.

2. The strain according to claim 1, wherein the strain has a linear shape with a length of 0.5 to 3 cm.

3. The strain according to claim 1, wherein the strain is able to survive in a medium containing NH$_4$Cl in an amount of 0.4 g/L or less.

4. The strain according to claim 1, wherein the strain can be harvested through a sieve having a mesh size of 0.1 to 1.0 mm.

5. A method for harvesting a *Spirulina* strain, comprising the step of passing an *Arthrospira platensis* NCB002 strain having a linear shape and deposited with accession number KCTC 13731BP through a sieve having a mesh size of 0.1 to 1.0 mm.

6. The method according to claim 5, wherein the strain has a linear shape with a length of 0.5 to 3 cm.

7. The method according to claim 5, wherein the strain is able to survive in a medium containing NH$_4$Cl in an amount of 0.4 g/L or less.

* * * * *